(12) United States Patent
Devlin, Sr. et al.

(10) Patent No.: US 7,229,592 B2
(45) Date of Patent: Jun. 12, 2007

(54) METHOD FOR REPLACING USED REACTION CUVETTES IN AN AUTOMATIC ANALYZER DEPENDING UPON NEXT SCHEDULED ASSAY

(75) Inventors: William Jackson Devlin, Sr., Lincoln University, PA (US); Stephen Lawrence Frye, Newark, DE (US); David Jeffrey Miller, Wilmington, DE (US); Thomas John Pankratz, Newark, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 11/229,812

(22) Filed: Sep. 19, 2005

(65) Prior Publication Data

US 2006/0008384 A1   Jan. 12, 2006

Related U.S. Application Data

(62) Division of application No. 10/318,804, filed on Dec. 13, 2002, now Pat. No. 6,991,764.

(51) Int. Cl.
  *G01N 21/00* (2006.01)
(52) U.S. Cl. .............................. 422/67; 422/63; 422/64; 422/99; 422/100; 436/50; 436/55

(58) Field of Classification Search ................. 422/60, 422/65, 99–100, 63, 64, 67; 436/180, 50, 436/55
See application file for complete search history.

(56) References Cited

U.S. PATENT DOCUMENTS

| | | | |
|---|---|---|---|
| 4,720,374 A | | 1/1988 | Ramachandran |
| 4,785,407 A | * | 11/1988 | Sakagami ..................... 702/22 |
| 5,100,622 A | | 3/1992 | Mimura et al. |
| 5,482,861 A | | 1/1996 | Clark et al. |
| 5,575,976 A | | 11/1996 | Chpoerena et al. |
| 5,679,309 A | | 10/1997 | Bell |
| 5,741,461 A | | 4/1998 | Takahashi et al. |
| 5,876,668 A | | 3/1999 | Kawashima et al. |
| 6,027,691 A | | 2/2000 | Watts et al. |

* cited by examiner

*Primary Examiner*—Jill Warden
*Assistant Examiner*—Jyoti Nagpaul
(74) *Attorney, Agent, or Firm*—Leland K. Jordan (57) ABSTRACT

A method for determining not to reuse a previously used and cleaned reaction cuvette in an analyzer when an assay scheduled to be performed may be adversely affected by contaminants remaining in the cleaned reaction cuvette. If determined not to reuse a previously used and cleaned reaction cuvette, the previously used and cleaned reaction cuvette is replaced with an unused new reaction cuvette.

2 Claims, 6 Drawing Sheets

METHOD FOR REPLACING USED REACTION CUVETTES IN AN AUTOMATIC ANALYZER DEPENDING UPON NEXT SCHEDULED ASSAY

This application is a Divisional of U.S. Ser. No. 10/318,804 filed on Dec. 13, 2002 now U.S. Pat. No. 6,991,764.

FIELD OF THE INVENTION

The present invention relates to a method and apparatus for automatically processing a patient's biological fluids such as urine, blood serum, plasma, cerebrospinal fluid and the like. In particular, the present invention provides a method to determine whether or not to reuse a reaction cuvette in a analyzing system by considering the identity of an assay scheduled to be next performed therein.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain endpoint or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing pressures on clinical laboratories to reduce cost-per-reportable result, there continues to be a need for improvements in the overall cost performance of automated clinical analyzers. In particular, sample analysis continuously needs to be more cost effective in terms of reducing consumables or the cost thereof required for each and every reaction assay.

One contributor to reducing cost-per-reportable result is the ability to repeatedly perform reaction assays in reaction cuvettes that are washed or otherwise cleaned after a first reaction is completed and between subsequent reaction assays. What has been overlooked, however, in many such cleaning systems, is that washing techniques are not fully capable of restoring a cleaned used cuvette to the degree of cleanliness of an unused cuvette. Thus, reagent residues for a prior reaction assay may be present in a washed reaction cuvette. Certain highly sensitive assays may be caused to have inaccurate results if certain reagent residues from preceding reaction assays are present in a re-washed reaction cuvette. One solution is to simply use a new reaction cuvette for each new assay however this defeats the desire to achieve lower costs-per-reportable result.

U.S. Pat. No. 5,741,461 discloses a sample analysis system having means for judging in advance of sample addition whether any of a plurality of reaction cuvettes located between a cleaning position and the sample addition position should be cleaned when the analyzer starts to operate.

U.S. Pat. No. 5,679,309 discloses an automatic analyzing apparatus having first and second wash complement cuvettes positioned at a wash point when reactant is added at first and second reactant addition points to the target cuvette. Once the wash complements are determined, the analyzer compares the complements with the inventory of wash designated cuvettes. If the first wash complement is designated for wash, the controller indexes and parks the reaction carousel for reactant addition at the first addition point to the targeted cuvette while simultaneously and opportunistically washing of the first wash complement cuvette. If the first wash complement cuvette is not ready to be washed but the second wash complement cuvette is, the analyzer indexes and parks the reaction carousel for addition of reactant to the targeted cuvette at the second reactant addition point and simultaneously and opportunistically washing of the second wash complement cuvette. If neither of the first or second wash complement cuvettes are ready for wash, no washing occurs and the analyzer indexes and parks the targeted cuvette at the first reaction addition point and reactant is added.

U.S. Pat. No. 6,027,691 discloses a cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the internal chamber of the cuvette wash station probe for removing waste liquids from a cuvette disposed within the random access analyzing station at the analyzing site and for transferring such waste liquids to a disposal site.

From this discussion of the art state in automated clinical analyzers, it may be seen that while has been considerable progress has been made toward increasing assay processing efficiency, there remains an unmet need for a method for determining whether or not washing and reusing a reaction cuvette in an analyzer can be done without sacrificing assay quality. In particular, there remains an unmet need for determining not to reuse a cleaned reaction cuvette when the assay scheduled to be next performed in said cleaned reaction cuvette may be adversely affected by reagents employed in the assay previously performed in said cleaned reaction cuvette.

SUMMARY OF THE INVENTION

The principal object of the invention is to provide an automated method for determining not to reuse a cleaned used reaction cuvette in an automated analyzer whenever an assay scheduled to be next performed in said cleaned used reaction cuvette might be adversely affected by any contaminants remaining from the assay or assays previously performed in said cleaned used reaction cuvette. In addition, the analyzer is controlled so that whenever certain assays are scheduled to be performed in a cleaned used reaction cuvette, the cleaned used reaction cuvette is automatically removed, discarded, and replaced with a fresh, unused reaction cuvette. The analyzer may be optionally controlled so that whenever an assay is scheduled to be performed in a cleaned used reaction cuvette, and the same assay was previously performed in said cleaned used reaction cuvette and the assay results are outside normal test ranges, the cleaned used reaction cuvette is automatically removed, discarded, and replaced with a fresh, unused reaction cuvette. The analyzer typically includes a circular rotatable assay reaction carousel for holding assay reaction cuvettes and providing stepwise movements in a circular direction at a constant velocity, the stepwise movements being separated by stationary dwell times, during which dwell time an assay device may operate on an assay mixture contained within a reaction cuvette. An analyzer like those on which the present invention may be performed typically has a plurality of conventional assay operation stations at which are positioned individual assay devices, such as sensors, reagent add stations, mixing stations, separation stations, and the like.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
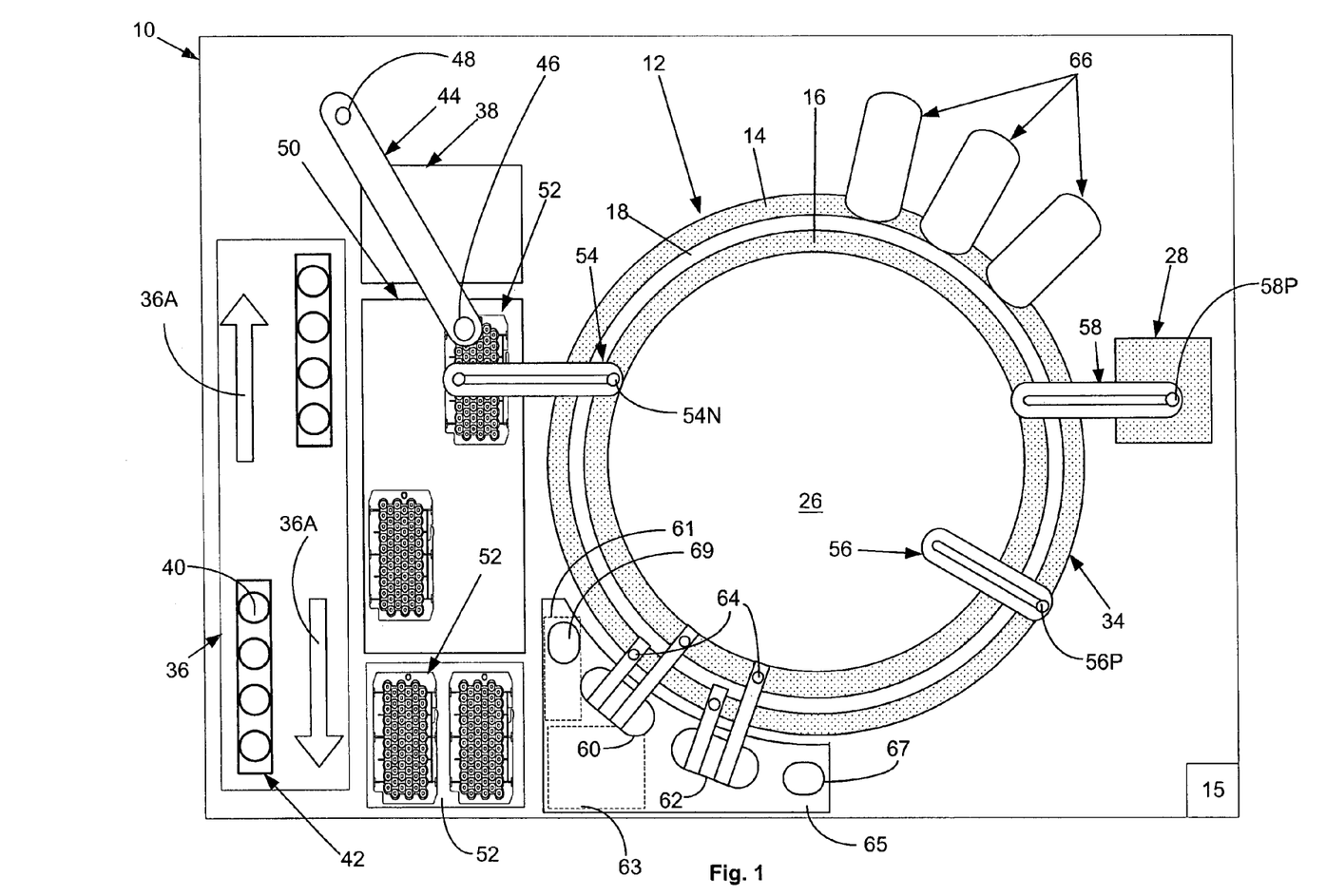
FIG. 1 is a schematic plan view of a single conventional automated clinical analyzer like those known in the art.
Figure 2:
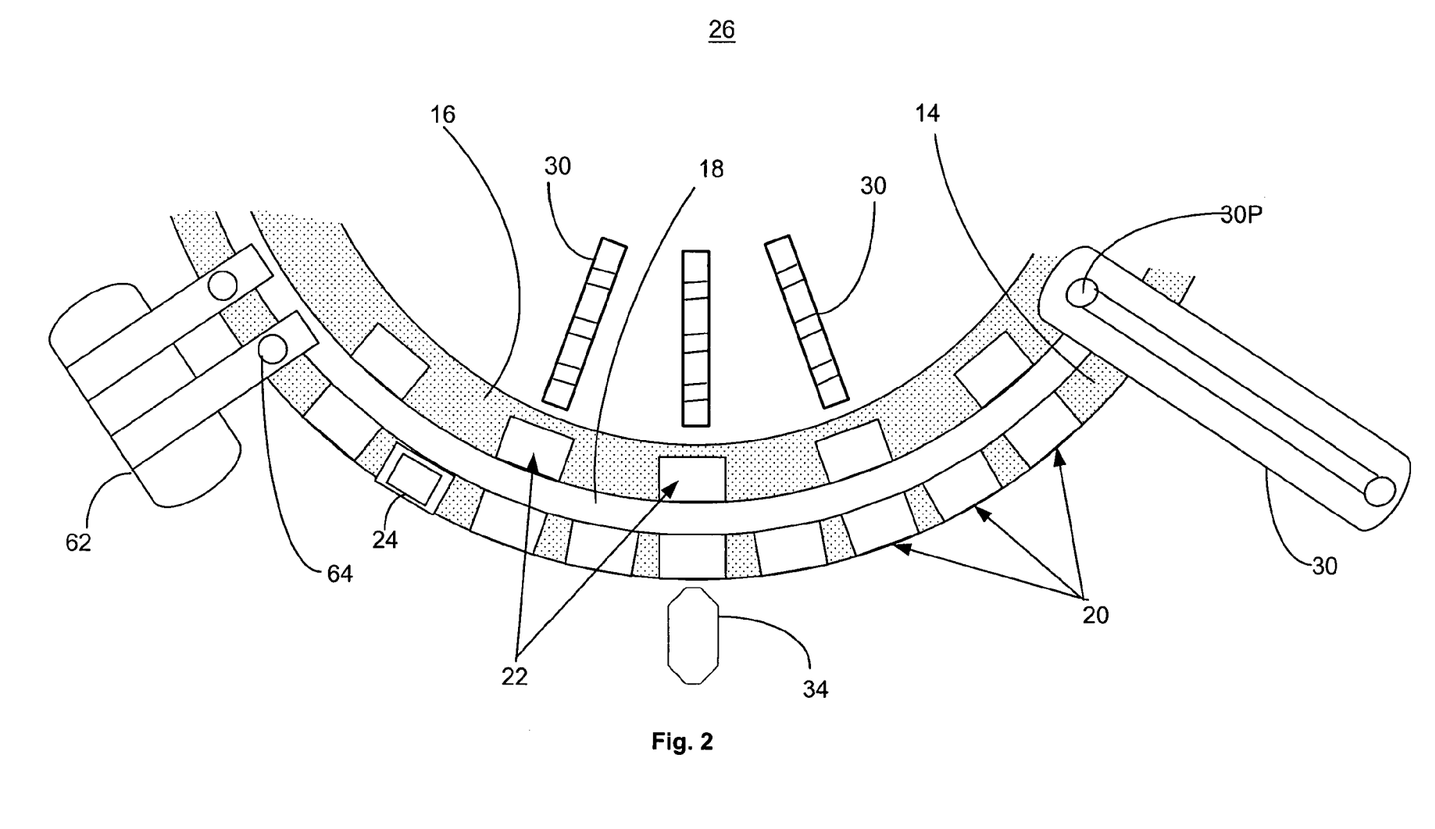
FIG. 2 is an enlarged partial schematic plan view of the automated analyzer of FIG. 1.
Figure 5:
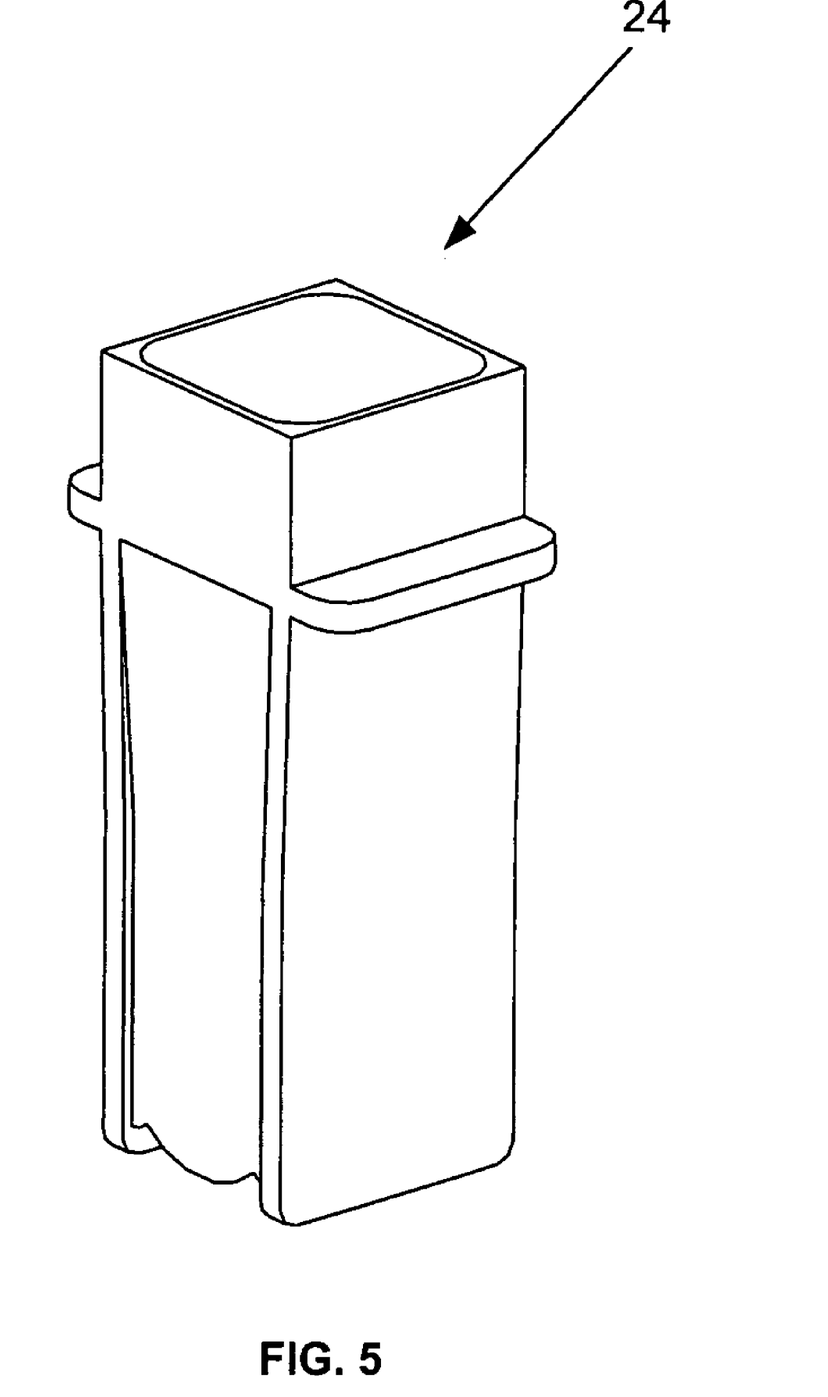

FIG. 1, taken with FIG. 2, shows schematically the elements of a single conventional automatic chemical analyzer 10 convenient for practicing the present invention and comprising a reaction carousel 12 supporting an outer cuvette carousel 14 of cuvette ports 20 and an inner cuvette carousel 16 of cuvette ports 22, the outer cuvette carousel 14 and inner cuvette carousel 16 being separated by a open groove 18. Cuvette ports 20 and 22 are adapted to receive a plurality of reaction cuvettes 24 typically formed as small, flat walled, U-shaped containers (see FIG. 5) with an open central reaction portion closed at the bottom and with an opening at the top of the cuvettes 24 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 24.

Two temperature-controlled reagent storage areas 26 and 28 each store a plurality of reagent cartridges 30, cartridges 30, for example being a multi-compartmented reagent container like those described in U.S. Pat. No.: 4,720,374, or co-pending application Ser. No.: 09/949,132 assigned to the assignee of the present invention, and sold under the tradename FLEX™ cartridge by Dade Behring Inc, Deerfield, Ill., and containing reagents as necessary to perform a given assay. A selectively-opened lid (not shown) covers each of reagent storage areas 26 and 28 to allow access to cartridges 30; for simplicity, only three reagent cartridges 30 are schematically illustrated in FIG. 2 as disposed beneath a cut out portion of reagent storage area 26 however similar reagent cartridges 30 are disposed within reagent storage area 28. Shuttle means (not shown) move individual cartridges 30 to access ports for reagent probes 56P and 58P discussed later. Storage area 28 may be conveniently located external to the circumference of outer cuvette carousel 14 and reagent storage area 26 may be conveniently located internal to the circumference of inner cuvette carousel 16.

A clinical analyzer 10 like those on which the present invention may be performed has a plurality of conventional assay operation devices 34 disposed proximate carousel 12 and at which are positioned individual computer controlled electro-mechanical devices, such as sensors, reagent add stations, mixing stations, and the like, as required to perform the myriad of actions required in well known clinical assays. Such devices and their operational control by a microprocessor based computer 15 are well known in the art and need not be described herein. See, for example, U.S. Pat. Nos. 5,876,668, 5,575,976, and 5,482,861 and the references cited therein.

An indexing drive for the reaction carousel moves the reaction cuvettes in the constant direction a predetermined numbers of incremental steps. The length of the circumference of cuvette carousels 14 and 16, the separation distance between cuvette ports 20 and 22, the number of cuvette ports 20 and 22, and the number of increments per indexing are selected so that any given cuvette ports 20 and 22 returns to its original starting position after a fixed number of incremental steps. Thus, all cuvette ports 20 and 22 on the reaction carousel 12 return to their original location in a full operational cycle time which is determined by the fixed number of incremental steps multiplied by the sum of dwell time at each assay device and the time required for a stepwise movement. This predetermined movement cycle facilitates the precise tracking by computer 15 of each and every cuvette port 20 and 22 and reaction cuvettes 24 contained therein, including having historical data concerning the types of assays conducted in each and every reaction cuvette 24.

Figure 3A:
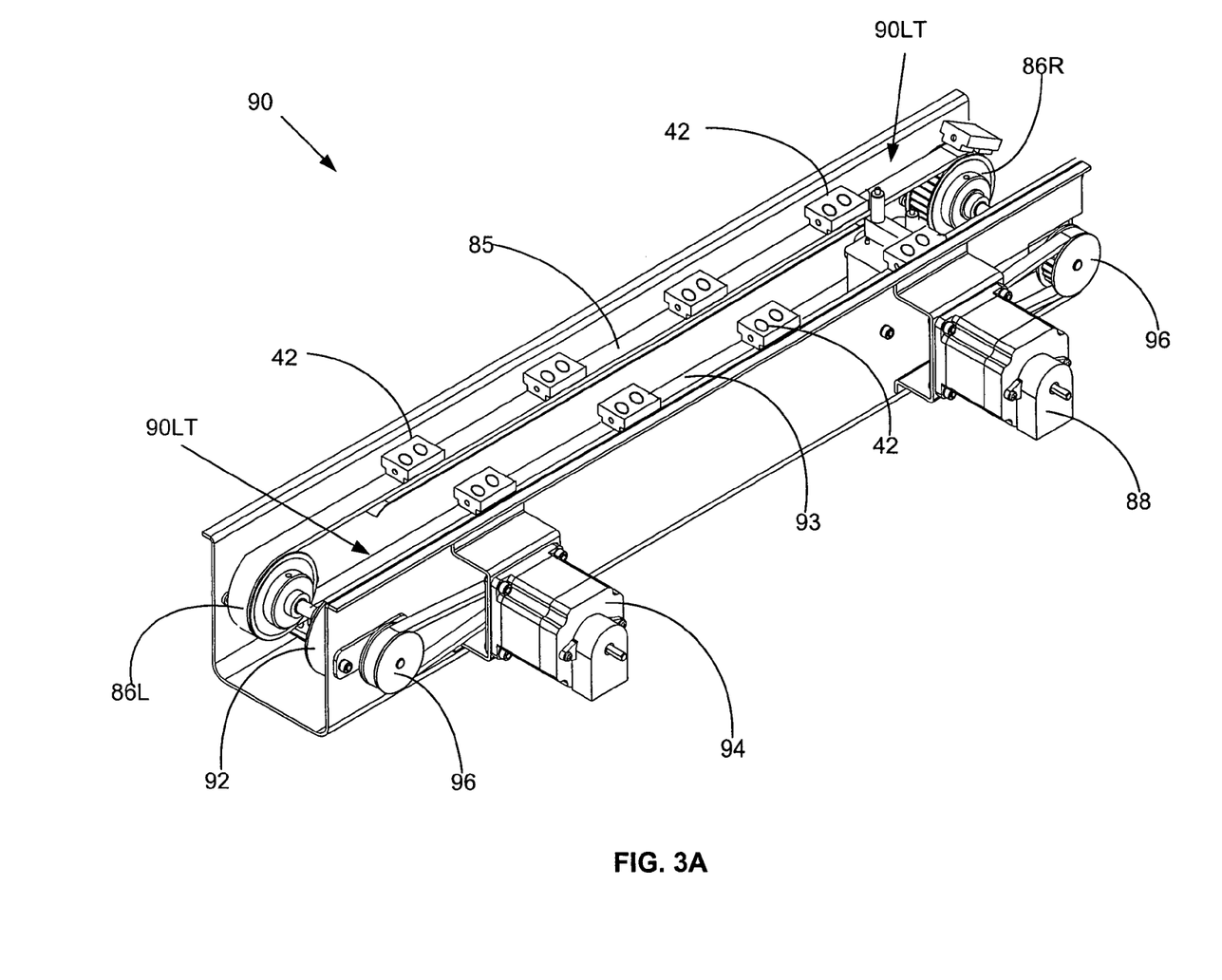
FIGS. 3A and 3B are perspective view of a sample rack transport system useful in practicing the present invention; and, FIG. 4 is a perspective view of a multi-well aliquot cuvette useful in practicing the analyzer of FIG. 1; and, FIG. 5 is perspective view of a reaction cuvette useful in practicing the present invention.
Figure 3B:
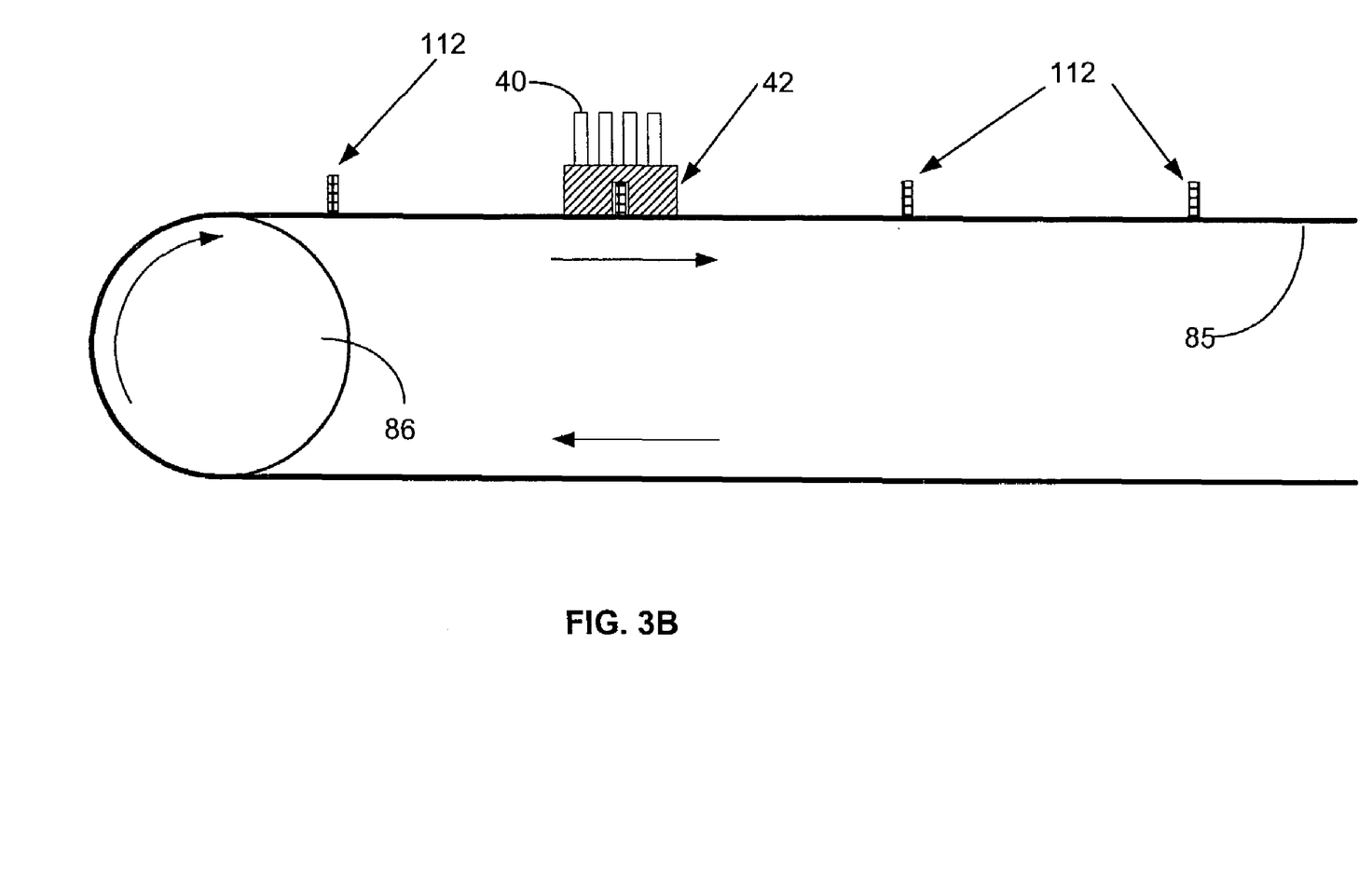

Incoming sample specimens to be tested are contained in sample tubes 40 mounted in sample tube racks 42 and transported into the arc of sampling arm 44, for example, by a bi-directional incoming and outgoing sample tube transport system 36, as indicated by open arrows 36A, and as described in co-pending application Ser. No.: 09/992,917 assigned to the assignee of the present invention. A magnetic drive system 90 useful in analyzer 10 is seen in the perspective drawings of FIG. 3A to comprise at least one bi-directional linear drive transport mechanism 90LT depicted, for example, as a first belt 85 endlessly circulating around a first pair of pulleys 86, one of the first pulleys 86 being coupled to a first bi-directional motor 88, the first belt 85 and first pulleys 86 being mounted beneath and in close proximity to the operating surface of analyzer 10 which defines input and output lanes. First belt 85 is driven by motor 88 in an incoming direction, for example along the direction of arrow 36A, and is located beneath the operating surface of analyzer 10. In a similar manner, magnetic drive system 90 comprises a second belt 93 endlessly circulating around a second pair of pulleys 92, one of the second pulleys 92 (only one such pulley 92 is visible) being coupled to a second bi-directional motor 94, the second belt 93 and second pulleys 92 being mounted beneath and in close proximity to the output lane 74 portion of the operating surface of analyzer 10. Second belt 93 is driven by second motor 94 in a second direction opposite to the first direction. FIG. 3B illustrates a plurality of sample tube racks 42 coupled to each drive belt 85 and 93 by means of a plurality of upright posts 112 generally equally spaced apart by a predetermined distance, and, as seen in FIG. 3B, the plurality of upright posts 112 are attached to belts 85 and 93 at that same predetermined distance. Posts 112 are adapted by any of various mechanical techniques, such as screws, snaps, welds, etc., to secure the plurality of magnetic sample tube racks 42 to belt 85 and 93.

After sample has been aspirated by sampling arm 44 described next and deposited within aliquot wells 52W, sample tube racks 42 may optionally be inventoried within analyzer 10 inside an environmental chamber 38 as described in co-pending application Ser. No.: 09/827,045 also assigned to the assignee of the present invention. Patient liquid specimens contained in open sample tubes 40 are identified by reading bar coded indicia placed thereon using a conventional bar code reader to determine, among other items, a patient's identity, the tests to be performed, if a sample aliquot is desired to be retained inside environmental chamber 38 and if so, for what period of time. It is also common practice to place bar coded indicia on sample tube racks 42 and employ a large number of conventional bar code readers installed throughout analyzer 10 in order to ascertain, control and track the location of both sample tubes 40 and sample tube racks 42. Such reader devices and the techniques for tracking are well known in the art and are not seen in FIG. 1 nor need be discussed further.

Figure 4:
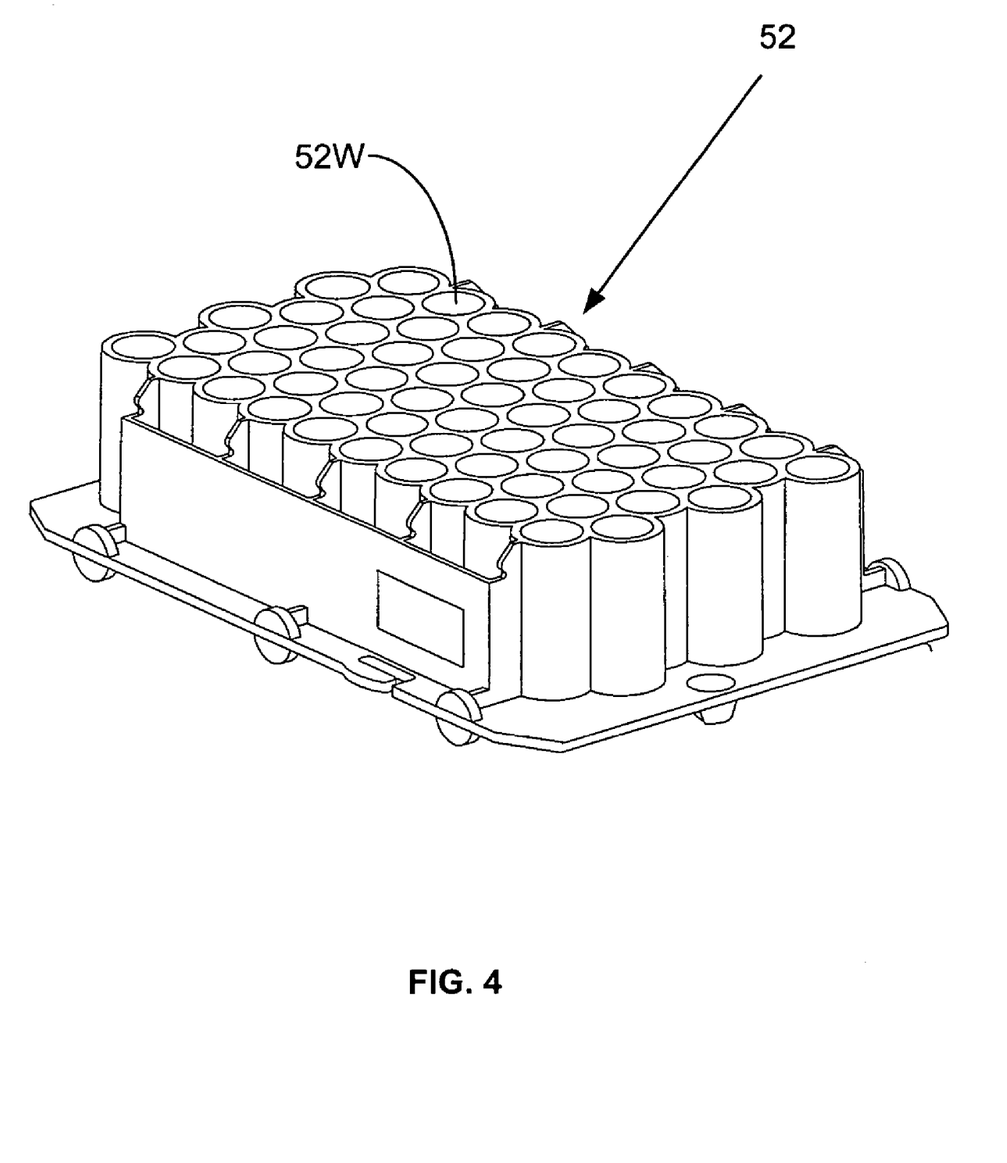

A fluid sampling arm 44 supports a conventional liquid sampling probe 46 and is mounted to a rotatable shaft 48 so that movement of sampling arm 44 describes an arc intersecting the sample tube transport system 36 and an aliquot strip transport system 50 adapted to transport multi-well aliquot cuvettes 52, like that seen in FIG. 4, to a conventional sample/reagent aspiration and dispense arm 54 located proximate reaction carousel 12. Sampling arm 44 is operable to aspirate liquid sample from sample tubes 40 and to dispense a sample aliquot into one or more of a plurality of aliquot wells 52W in aliquot cuvettes 52, depending on the quantity of sample required to perform the requisite assays and to provide for a sample aliquot to be retained by analyzer 10 within environmental chamber 38. Another sample aspiration and dispense arm 54 is controlled by computer 15 and is adapted to aspirate a controlled amount of sample from wells 52W via a conventional nozzle 54N and to dispense an appropriate amount of aspirated sample into one or more cuvettes 24 for assay testing for one or more analytes. After sample has been dispensed into reaction cuvettes 24 in cuvette ports 20 and 22, conventional transfer means move aliquot strips 52 as required between aliquot strip transport system 50 and environmental chamber 38 or, optionally, to a waste disposal area, not shown.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing analytical assays conducted by analyzer 10 in patient samples. In particular, computer 15 is programmed with analyzer control commands that record in memory the identity of all assays preformed in cuvettes 24, the identity of all individual cuvettes 24 as they are transported throughout analyzer including their condition as cleaned used, the test results of assays conducted in individual cuvettes 24, normal (healthy) patient test ranges for assays analyzer 10 is adapted to conduct, and the like as required for performing the various embodiments of the present invention. At least two reagent aspiration and dispense arms 56 and 58 comprising a pair of conventional liquid reagent probes, 56P and 58P, respectively, are independently mounted and translatable between reagent storage areas 36 and 28, respectively. Probes 56P and 58P are shown in FIG. 1 in two operating positions, with one probe, 56P, adapted to remove reagent from a reagent container in storage area 26 and to dispense aspirated reagent into cuvettes 22 and 24 located in cuvette carousels 14 and 16 and with the other probe, 58P, adapted to remove reagent from a reagent container in storage area 28 and to dispense aspirated reagent into cuvettes 22 and 24 located in cuvette carousels 14 and 16. Probes 56P and 58P typically comprise an ultrasonic mechanism used for hydrating, aspirating, dispensing and mixing reagents. The hydrating, aspirating, dispensing and mixing mechanisms have features well known in the art and need not be described further.

Cuvette load and unload stations 60 and 62, respectively, are positioned proximate outer cuvette carousel 14 and are conventionally adapted to load cuvettes 24 into cuvette ports 20 and 22 seen in FIG. 2 formed in outer cuvette carousel 14 and inner carousel 16, and to unload used cuvettes 24 from cuvette ports 20 and 22 after an assay has been completed therein, using for example a translatable robotic arm 64 with a conventional clamping mechanism (not shown) on each of load and unload stations 60 and 62. In operation, all used cuvettes 24, cuvettes 24 in which an assay has been finally conducted, are removed from cuvette ports 20 and 22 and replaced with cleaned used cuvettes 24. Subsequent assays are conducted in cleaned used cuvettes 24 unless dictated otherwise by the present inventive method for determining not to reuse a previously cleaned used reaction cuvette. Unloaded cleaned used cuvettes 24 are deposited into a cuvette wash station 65 by translatable robotic clamp 64. Cuvette load and unload stations 60 and 62, respectively, are rotatably mounted within analyzer 10 to facilitate such load and unload operations. In a typical cleaning embodiment, cuvette wash station 65 comprises stationary sources of pulsed jet streams of a cleaning detergent in heated water, pulsed jet streams of distilled rinsing water, and continuous streams of dry air directed into the interior of reaction cuvettes 24 carried in multiple openings along a step-wise moving belt. In such a cuvette wash station 65, translatable robotic arm 64 portion of unload station 62 removes used cuvettes 24 from cuvette ports 20 and 22 and moves a stream of reaction cuvettes 24 into wash station 65 through port opening 67; computer 15 records the identity of assays previously conducted in each used cuvette 24. The used cuvettes 24 enter into cuvette wash station 65 and after being washed and dried, cleaned used cuvettes 24 are inventoried in a controlled known location within cleaned used cuvette store 61 (dashed lines for clarity) along with the identity of assays previously conducted therein. Cleaned used cuvettes 24 may be inventoried for example, in a continuously circulating serpentine track having inventory slots for storing cleaned used cuvettes 24, and are thereby accessible through an opening 69 to cuvette load station 60. Herein, the term "cleaned" refers to a cuvette that has been subjected to such washing and drying operations. Unused, new cuvettes 24 that have never been used in a reaction assay are originally placed in inventory by an operator in new cuvette store 63 (dashed lines for clarity) from which cuvette load station 60 may also access new cuvettes 24 when dictated by the present invention. Conventional sample processing devices 34 (FIG. 2), are positioned at selected circumferential locations about the reaction carousel 12 in order to access reaction cuvettes 26. Processing devices 34 are adapted to provide, among other processing steps, for mixing together of the sample liquid and the reagent liquid contained in cuvettes 24, for mixing the sample liquid and the reagent liquid contained in cuvettes 24, and for magnetic separation of tagged magnetic particles from free tags or reagent liquid contained in cuvettes 24.

Various assay analyzing stations 66 may be located proximate outer reaction carousel 12 and are adapted to measure light absorbence in or emission from cuvettes 24 at various wavelengths, from which the presence of analyte in the sample liquid may be determined using well-known analytical techniques. Stations 66 typically comprise conventional photometric, fluorometric or luminescent measuring devices adapted to perform an interrogating measurement at any convenient time interval during which reaction carousel 12 is stationary.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

In operation of analyzer 10 like seen in FIG. 1, and in accord with the present invention, either a previously cleaned used cuvette 24 that has been washed clean or a new unused cuvette 24 may be used for each and every reaction assay sample analysis. For reasons of reducing the cost-per-reportable result, it is advantageous that used cuvettes 24 be washed in a cuvette wash station 65, stored in a cleaned used cuvette store 61 and replaced into cuvette ports 20 and 22 to be re-cleaned after being used on subsequent reaction assays. However, washing techniques that are feasible for installation on automated analyzers 10 cannot ensure that all vestiges of liquid contamination possibly remaining in a washed cleaned cuvette 24 are totally removed, thereby making it possible for extremely small residues of reagents or other possible contaminants to be present in a cleaned used cuvette 24. Unfortunately, certain highly sensitive assays may have inaccurate results if conducted in a reused cuvette 24 having any amount of contaminants from a preceding assay are present in a cleaned used cuvette. One solution to such a problematic situation is to use a fresh new cuvette 24 for every new assay to be performed by analyzer 10. Such a solution invokes the expense of a new cuvette 24 for every assay. According to the present invention, rather than always using fresh cuvettes 24 or always reusing washed cuvettes 24 and incurring risk of assay inaccuracies from possible contaminants, the present invention predefines what may be called "illegal A–B pairs" of assays. Herein, the terms "A assays" and "B assays" are not necessarily descriptive of the type or analyte sensitivity of an assay but are used as a matter of convenience to designate that two different assays are simply two different assays. Thus, an A–B pair of assays are two different assays paired together for the sake of comparison as described herein.

An illegal A–B pair of assays is defined as all ordered pairs of assays A and B created whenever any amount of the reagents used in an A assay remained in a cuvette 24 after that particular cuvette 24 was used to conduct an A assay and subsequently washed in cuvette wash station 65, and if the presence of such remaining A assay reagent is known or was determined to adversely affect analytical results of a B assay to be immediately subsequently carried out in that particular cleaned used cuvette 24, then an illegal A–B pair is created. For reasons of analytical accuracy, in accordance with a key feature of the present invention, in the event an illegal A–B pair is formed, it is not permissible to conduct a B assay in a cuvette 24 that has just previously been used to conduct an A assay even if cuvette 24 has been cleaned. In other words, consider that a singluated stream of assays are scheduled to be performed in a single cleaned used reaction cuvette 24CU; the present invention thus requires that, in the event an illegal pair A–B is created between one assay (the B assay) and the preceding next adjacent assay (the A assay), then the B assay must be conducted in a fresh new reaction cuvette 24 and not in the cleaned used reaction cuvette 24CU. On the other hand, if a B assay is scheduled to be performed in a cleaned used cuvette 24, an illegal pair A–B is not created even if an A assay has previously been performed in that cleaned used cuvette 24CU but that A assay was not the next adjacent assay immediately preceding the B assay. Such a situation may arise because the present invention provides for a single reaction to be cleaned and re-used multiple numbers of times, until an illegal A–B pair is formed or, optionally, until a predetermined upper limit of cleaning steps is reached. In this case, the B assay may be conducted the cleaned used reaction cuvette 24CU because the A assay was not the next adjacent assay immediately preceding the B assay.

In an optional embodiment of the present invention, analyzer 10 may be controlled by computer 15 so that whenever an assay is scheduled to be performed in a cleaned used reaction cuvette 24, and the same assay was previously performed in that same cleaned used reaction cuvette 24 and the assay results fell outside normal test ranges by more than a predetermined range, percentage or other error indicator, the cleaned used reaction cuvette 24CU is automatically removed, discarded, and replaced with a fresh, unused reaction cuvette 24. This alternate method for determining not to reuse a cleaned used reaction cuvette in an automated analyzer when an assay scheduled to be next performed in the cleaned used reaction cuvette is the same assay as previously immediately performed in said cleaned used reaction cuvette ensures test accuracy of the scheduled assay by replacing the cleaned used reaction cuvette with a new cuvette if the results of the previously performed assay are materially different than the norm of "expected" test results determined for a number of "normal" patient samples for said assay.

In a further optional embodiment of the present invention, analyzer 10 may be controlled by computer 15 so that whenever any one of a group S of predefined highly sensitive assays is scheduled to be performed in a cleaned used reaction cuvette 24, the cleaned used reaction cuvette 24 is required to be automatically removed, discarded, and replaced with a fresh, unused reaction cuvette. In other words, if a B assay falls within this group S of predefined highly sensitive assays, than all assays analyzer 10 is adapted to conduct become A assays and an illegal A–B pair is defined.

Another key feature of the invention is that if any assay other than an A assay has been conducted in a cleaned used cuvette 24, and the cuvette 24 has being washed in cuvette wash station 65, then assay B may be safely completed in cleaned used cuvette 24.

In operation, cuvette load station 60 is automatically operated to load all cuvette ports 20 and 22 with cleaned used cuvettes 24 already washed in cuvette wash station 65 and stored in cleaned used cuvette store 61. As every new assay B is scheduled on analyzer 10, computer 15 determines the identity of the next available cleaned used cuvette 24 to ascertain which reaction assay has been immediately previously conducted therein and determines if that assay is classified as an A assays. If the next adjacent assay immediately preceding the B assay is not classified as an A assay, the new assay B is automatically conducted in that next available cleaned used cuvette 24 previously taken from cleaned used cuvette store 61 and loaded into cuvette port 20 or 22. In contrast, if the next adjacent assay immediately preceding the B assay conducted in the next available cleaned used cuvette 24 is determined to be classified as an A assay, computer 15 compares the identity of the B assay with all of its corresponding illegal A–B pairs in a look-up-table containing a listing of all illegal A–B pairs, like seen in Table 1. If the new B assay has no corresponding illegal A–B pair, then the new assay B is automatically conducted in that next available cleaned used cuvette 24. If the new B assay forms an illegal A–B pair from the listing of all illegal A–B pairs, then that next available cleaned used cuvette 24 is automatically removed from either cuvette port 20 or 22 by cuvette unload station 62, disposed into a trash dump, and is automatically replaced with an unused, fresh cuvette 24 taken by cuvette load station 60 from new cuvette store 63. Thusly, in operation, all used cuvettes 24 are removed from cuvette ports 20 and 22 and replaced with cleaned used cuvettes 24. Subsequent assays are conducted in cleaned used cuvettes 24 unless dictated otherwise by the present inventive method for determining not to reuse a previously used and washed reaction cuvette by defining illegal A–B pairs of assays such that if an A assay was scheduled to be conducted in a cuvette immediately previously used for conducting a B assay, the A assay would instead be conducted in a new cuvette. As mentioned before, however, a group S of highly sensitive assays may be defined such that if a B assay falls within this group S of assays, then a next available cleaned used cuvette 24 is automatically replaced with an unused, fresh cuvette 24.

An important feature of the method is a unique "look-up" table like the one in Table 1 embedded within computer 15 and cleaned used to identify illegal A–B pairs and manage the useage of new or cleaned used cuvettes 24, as explained above.

TABLE 1

| Assay A | Assay B |
| --- | --- |
| TRIGLYCERIDES | LIPASE |
| UREA | TRIGLYCERIDES |
| URIC ACID | TRIGLYCERIDES |
| CREATINE KINASE-MB | TRIGLYCERIDES |
| AMYLASE | TRIGLYCERIDES |
| AMMONIA | TRIGLYCERIDES |
| LACTIC ACID | TRIGLYCERIDES |
| ALKALINE PHOSPHATASE | MAGNESIUM |
| CREATINE KINASE | MAGNESIUM |
| PSEUDOCHOLINESTERASE | PHOSPHORUS |
| THEOPHYLLINE | PHOSPHORUS |
| C-REACTIVE PROTEIN | PHOSPHORUS |
| PHENYTOIN | PHOSPHORUS |
| ETHYL ALCOHOL | AMMONIA |
| ETHYL ALCOHOL | PRETEIN-URINE, CSF |
| PRETEIN-URINE, CSF | TOTAL BILIRUBIN |
| LACTIC ACID | LACTIC DEHYDROGENASE |
| TOTAL PROTEIN | TOTAL BILIRUBIN |
| ASPARTATE AMINOTRANSFERASE | LACTATE DEHYDROGENASE |
| ALANINE AMINOTRANSFERASE | LACTATE DEHYDROGENASE |
| CARBAMAZEPINE | URINE AMPHETAMINE |
| CARBAMAZEPINE | URINE BARBITUATE |
| CARBAMAZEPINE | URINE BENZODIAZEPHEN |
| CARBAMAZEPINE | URINE COCAINE |
| CARBAMAZEPINE | URINE METHAMPHETAMINE |

For the purpose of illustration only, consider an example of the present invention in which a new assay to be conducted by analyzer 10 is a TRIG assay and the next available cleaned used cuvette 24 is identified by computer 15 to have previously had GLU and PSA assays conducted therein. Since neither GLU nor PSA are found in Table 1 as an A assay, it is permissible for that TRIG assay to be conducted in the next available cleaned used cuvette 24. In contrast, if the next available cleaned used cuvette 24 in which the new TRIG assay is scheduled to be conducted was identified by computer 15 to have previously had any one of a BUN, URCA, CKMB, AMY, AMON, or LA assay conducted therein as the next adjacent assay immediately preceding the B assay, then an illegal A–B pair is identified by computer 15 for the new TRIG assay and it is not permissible for that TRIG assay to be conducted in the next available cleaned used cuvette 24. Further, in this same example, if the next available cleaned used cuvette 24 in which the new TRIG assay might be conducted was identified by computer 15 to have previously had an ALP, CK and PCHE assays conducted therein, then even though these ALP, CK and PCHE assays are A assays, that do not form an illegal A–B pair for new that TRIG assay and it is permissible for that new TRIG assay to be conducted in the next available cleaned used cuvette 24.

Another example of the present invention exists when a new B assay to be conducted by analyzer 10 is a PSA assay. PSA assays are sufficiently sensitive to any form of contamination so that in this embodiment, PSA assays are predefined to form an illegal A–B pair with all assays analyzer 10 is adapted to conduct. Thus, the present invention provides for predefining certain sensitive B assays as forming an illegal A–B pair with all other assays the analyzer is adapted to conduct and requiring that the next available cleaned used reaction cuvette be automatically replaced with a new cuvette.

Another example of the present invention exists when a new B assay to be conducted by analyzer 10 is a TRIG assay and the assay previously immediately conducted in the next available cleaned used reaction cuvette 24 was also a TRIG assay. In this example, the analyzer control means 15 automatically determines not to reuse a cleaned used reaction cuvette 24CU if the results of the previously performed TRIG assay are materially different than the norm of "expected" TRIG test results determined for a number of "normal" or "healthy" patient samples. In this alternate embodiment, the TRIG assay results are outside normal test ranges by more than a predetermined value, percentage or other error indicator, and the cleaned used reaction cuvette 24CU may possibly still contain residues of exceptional TRIG levels. In order to ensure the accuracy of the next scheduled TRIG B-assay, the cleaned used reaction cuvette 24CU is automatically removed, discarded, and replaced with a fresh, unused reaction cuvette 24.

An important feature of the present invention is developing the list of illegal A–B pairs for the assays conducted by analyzer 10. One approach to developing the list of illegal A–B pairs consists of performing each and every "new" B assay that analyzer 10 is equipped to automatically perform in a new unused cuvette 24 and also performing each and every B assay in multiple cuvettes 24 each different one of which has been used to conduct "all other A assays" (all of those assays different than the "new" assay under evaluation that analyzer 10 is equipped to automatically perform) that analyzer 10 is equipped to automatically perform. If the analytical test results are identical, then it is concluded that no illegal A–B pairs exist for that "new" assay and it is permissible to conduct the "new" assay in a cleaned used cuvette 24. In contrast, if the analytical test results are not identical for certain ones of the all other assays, then illegal A–B pairs have been defined for that "new" assay and such certain ones of the all other assays, and it is not permissible to conduct the "new" assay in a cleaned used cuvette 24. As described before, in the event of an illegal A–B pair, the "new" B assay must be conducted in a new unused cuvette 24. While this is a tedious process for developing the list of illegal A–B pairs, it may be expedited if it is already known, from experience or chemical knowledge that certain reagents used in a B assay are adversely affected by reagents used in other assays immediately preceding the B assay; in such instances, illegal A–B pairs may be predefined to exist thereby aiding the development of the listing of illegal A–B pairs.

Another feature of the present invention already describes predefining certain extremely sensitive "B sensitive" assays as forming an illegal A–B pair with all other assays that analyzer 10 is equipped to automatically perform in which case it is not permissible to conduct the "B sensitive" assay in a cleaned used cuvette 24, regardless of which assays have been previously conducted in the next available cleaned used cuvette 24. For such extremely sensitive "B sensitive" assays, that next available cleaned used cuvette 24 is automatically removed from cuvette port 20 or 22, disposed of and automatically replaced with an unused, fresh cuvette 24.

Another feature of the present invention is optionally placing an upper limit upon the number of assays that may be conducted within the same cleaned used cuvette 24 irregardless of the absence of illegal A–B pairs or "B sensitive" assays. Although not necessary based on the information concerning illegal A–B pairs and "B sensitive" assays, such an upper limit may be set in the range of a maximum of about 50 assays may be conducted within the same cleaned used cuvette 24 as a matter of precaution.

In an even further optional embodiment of the present invention, since a small group of different assays make up a significant percentage of the totality of assays conducted by analyzer 10, said group herein identified by the letters SG, it is economically feasible to always use a fresh cuvette 24 whenever any assay other than an assay falling within the SG group of assays is scheduled to be conducted by analyzer 10. In such an event, the present invention predefines what may be called "legal D–E pairs" of assays and analyzer 10 may be controlled by computer 15 so that a legal D–E pair of assays is defined as all ordered pairs of assays D and E falling within the SG group of assays created such that whenever any amount of the reagents used in a D assay remained in a cuvette 24 after that particular cuvette 24 was used to conduct an D assay and subsequently washed in cuvette wash station 65, and if the presence of such remaining D assay reagent is known or was determined to not adversely affect analytical results of an E assay to be immediately subsequently carried out in that particular cleaned used cuvette 24, then a legal D–E pair is created. For reasons of analytical accuracy, in accordance with this feature of the present invention, in the event a legal D–E pair is formed, it is permissible to conduct a E assay in a cuvette 24 that has just previously been used to conduct an D assay even if cuvette 24 has been cleaned. In contrast, whenever any assay in the SG group of assays (the E assay) is scheduled to be conducted and any assay not in the SG group of assays has previously been immediately performed in that cleaned used cuvette 24CU, a legal D–E pair is not formed and that cleaned used cuvette 24CU is automatically removed, discarded, and replaced with a fresh, unused reaction cuvette 24.

In other words, consider that a singluated stream of assays are scheduled to be performed in a single cleaned used reaction cuvette 24CU; the present invention thus requires that, in the event a legal pair D–E is created between one assay in the SG group of assays (the E assay) and the preceding next adjacent assay also in the SG group of assays (the D assay), then the E assay may be conducted in the cleaned used reaction cuvette 24CU. On the other hand, if an E assay is scheduled to be performed in a cleaned used cuvette 24CU, a legal pair D–E is not created even if a D assay has previously been performed in that cleaned used cuvette 24CU but that D assay was not the next adjacent assay immediately preceding the E assay. Such a situation may arise because the present invention provides for a single reaction to be cleaned and re-used multiple numbers of times, until a legal D–E pair is not formed or, optionally, until a predetermined upper limit of cleaning steps is reached. In this case, the E assay may not be conducted in the cleaned used reaction cuvette 24CU because the D assay was not the next adjacent assay immediately preceding the D assay.

The use of predefined legal D–E assays as described hereinabove has the advantage of simplifying the amount of effort required to defined legal pairs since only a small number of the totality of different assays that can be conducted by analyzer 10 makes up group SG. Table 2 below contains a typical list of the small group of different assays that make up a significant percentage of the totality of assays conducted by analyzer 10, Table 2 also identifying some legal D–E pairs as examples only with an exemplary listing of typical clinical and immunoassays for the D and E assays. This listing is not intended to be definitive, exhaustive nor limiting in any manner. In practice, assays in Group D do comprise approximately 80–85% of the totality of assay tests requested to be performed by a typical automated clinical and immunoassay analyzers 10. It should be noted that the frequency of assays requested by a number of different physicians to be performed varies both regionally and demographically so that Table 2, while generally illustrative of actual clinical experience, is intended to be representative only. It should also be noted that a number of different methodologies are available for conducting the assays shown so that the actual determination of legal D–E pairs may be different for different analyzers.

TABLE 2

| D Assay | E Assay | Legal Pair |
|---|---|---|
| C-Reactive Protein | Glucose | YES |
| Glucose | Creatinine | YES |
| Creatinine | Glucose | YES |
| Urea Nitrogen | Calcium | YES |
| Calcium | Urea Nitrogen | YES |
| Alanine Aminotransferase | Aspartate Aminotransferase | NO |
| Aspartate Aminotransferase | Alanine Aminotransferase | NO |
| Total Bilirubin | Albumin | YES |
| Alkaline Phosphatase | Albumin | YES |
| Total Protein | Calcium | |
| Albumin | Uric Acid | |
| Cholesterol | Calcium | |
| Triglyceride | Urea Nitrogen | |
| Creatine Kinase | Glutamyl Transferase | NO |
| Uric Acid | Phosphorus | YES |
| γ-Glutamyl Transferase | Creatine Kinase | NO |
| Lactic Dehydrogenase | Creatine Kinase | NO |
| Direct Bilirubin | Uric Acid | YES |
| Phosphorus | Uric Acid | YES |
| HDL Cholesterol | Phosphorus | YES |

The details of performing a myriad of assays like those in Tables 1 and 2 within an analyzer system is a task regularly encountered within the art and need not be described herein. It is sufficient that the teachings of the present invention, that it may be automatically determining not to reuse a cleaned used reaction cuvette in an automated analyzer whenever an assay scheduled to be next performed in said cleaned used reaction cuvette might be adversely affected by any contaminants remaining from the assay or assays previously performed in said cleaned used reaction cuvette and various alternate embodiments. For these reasons, the present invention is not limited to those embodiments precisely shown and described in the specification but only by the following claims.

We claim:

1. An analytical analyzer adapted for automatically conducting clinical assays on patient samples in reaction cuvettes, said analyzer comprising:

a rotating reaction carousel supporting a cuvette carousel having cuvette ports adapted to receive a plurality of reaction cuvettes;

cuvette load and unload stations positioned proximate the cuvette carousel and adapted to load unused, new cuvettes into cuvette ports and remove cuvettes from cuvette ports;

a cuvette wash station accessible by said cuvette load and unload stations and adapted to wash used cuvettes, thereby providing cleaned used reaction cuvettes;

a new cuvette store accessible by said cuvette load stations and containing unused, new cuvettes; and, analyzer control means for determining if the assay scheduled to be next performed is an assay for triglycerides and the assay previously performed in said cleaned used reaction cuvette was an assay for at least one of urea, uric acid, creatine kinase-mb, amylase, ammonia or lactic acid, then requiring an unused reaction cuvette be used; or, determining if the assay scheduled to be next performed is an assay for magnesium and the assay previously performed in said cleaned used reaction cuvette was an assay for at least one of alkaline phosphatase or creatine kinase, then requiring an unused reaction cuvette be used; or, if the assay scheduled to be next performed is an assay for phosphorus and the assay previously performed in said cleaned used reaction cuvette was an assay for at least one of pseudocholinesterase, theophylline, c-reactive protein, or phenytoin, then requiring an unused reaction cuvette be used; or, if the assay scheduled to be next performed is an assay for ammonia or pretein-urine csf and the assay previously performed in said cleaned used reaction cuvette was an assay for at least ethyl alcohol, then requiring an unused reaction cuvette be used; or, if the assay scheduled to be next performed is an assay for total bilirubin and the assay previously performed in said cleaned used reaction cuvette was an assay for at least one of pretein-urine csf or total protein, then requiring an unused reaction cuvette be used; or, if the assay scheduled to be next performed is an assay for lactate dehydrogenase and the assay previously performed in said cleaned used reaction cuvette was an assay for at least one of lactic acid csf, aspartate aminotransferase or alanine aminotransferase, then requiring an unused reaction cuvette be used; or, if the assay scheduled to be next performed is an assay for urine amphetamine, urine barbituate, urine benzodiazephen, urine cocaine or urine methamphetamine and the assay previously performed in said cleaned used reaction cuvette was an assay for at least one of carbamazepine, then requiring an unused reaction cuvette be used; or, if the assay scheduled to be next performed is an assay for triglycerides and the assay previously performed in said cleaned used reaction cuvette was an assay for at least one of alkaline phosphatase, creatine kinase, or pseudocholinesterase, then requiring an unused reaction cuvette be used.

2. The analyzer of claim 1 further comprising optional analyzer control means for placing an upper limit upon the number of assays that may be conducted within the same cleaned used cuvette.

* * * * *